United States Patent [19]

Kasamatsu et al.

[11] 4,265,906
[45] May 5, 1981

[54] LOW MAMMALIAN TOXIC AND/OR LOW FISH TOXIC INSECTICIDES AND/OR ACARICIDES

[75] Inventors: Kiyoshi Kasamatsu, Takarazuka; Tadashi Ohsumi; Nobushige Itaya, both of Nishinomiya; Nobuo Ohno; Takashi Kato, both of Toyonaka, all of Japan

[73] Assignee: Sumitomo Chemical Company, Limited, Osaka, Japan

[21] Appl. No.: 96,212

[22] Filed: Nov. 20, 1979

[30] Foreign Application Priority Data

Nov. 22, 1978 [JP] Japan .................. 53-144709

[51] Int. Cl.$^3$ .............. A01N 53/00; C07C 121/75
[52] U.S. Cl. .............. 424/304; 260/465 D; 260/465 F
[58] Field of Search ............ 260/465 D; 424/304

[56] References Cited

U.S. PATENT DOCUMENTS

| | | | |
|---|---|---|---|
| 3,666,789 | 5/1972 | Itaya et al. | 560/124 |
| 3,973,036 | 8/1976 | Hirano et al. | 424/304 |

FOREIGN PATENT DOCUMENTS

| | | |
|---|---|---|
| 2615435 | 10/1977 | Fed. Rep. of Germany . |
| 51-95045 | 8/1976 | Japan . |
| 52-125145 | 10/1977 | Japan . |
| 1413491 | 11/1975 | United Kingdom . |

OTHER PUBLICATIONS

Mrak; "Advantages and Disadvantages of Pyrethrum", pp. 307-311 (1973).
Elliott et al., Nature, vol. 248, pp. 710-711 (1974).
Elliott et al., Nature, vol. 246, pp. 169-170 (1973).
Miyamoto, Environmental Health Perspectives, vol. 14, pp. 15-28 (1976).
Iwata et al., J. Econ. Ento., vol. 65, No. 3, pp. 643-644 (1972).
La Forge et al., J. Am. Chem. Soc., vol. 58, pp. 1777-1780 (1936).
Hilgetag, Preparative Organic Chemistry, pp. 875-877 (1972).
Smith, Organic Synthesis Collective, vol. 3, pp. 793-794 (1955).
Elliott et al., Pestic, Sci., vol. 5, pp. 791-799 (1974).
Wagner, Synthetic Organic Chemistry, pp. 546-547 and 558-559.

*Primary Examiner*—Dolph H. Torrence
*Attorney, Agent, or Firm*—Stevens, Davis, Miller & Mosher

[57] ABSTRACT m-(p-Bromophenoxy)-α-cyanobenzyl trans- or trans-rich-2,2-dimethyl-3-(2,2-dichlorovinyl)cyclopropanecarboxylate of the formula (I), and their preparation and use as a low fish toxic insecticide and/or acaricide.

5 Claims, No Drawings

LOW MAMMALIAN TOXIC AND/OR LOW FISH TOXIC INSECTICIDES AND/OR ACARICIDES

The invention relates to m-(p-bromophenoxy)-α-cyanobenzyl trans- or trans-rich-2,2-dimethyl-3-(2,2-dichlorovinyl)cyclopropanecarboxylate of the formula (I),

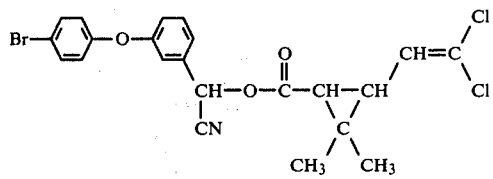

and their preparation and use as a low fish toxic insecticide and/or acaricide. The term "trans-rich" shows that the ratio of trans/cis is not less than 75/25.

An insecticide is one of the indispensable products for maintaining agricultrual products at a high level through the eradication of a wide variety of insect pests which inflict injuries upon agricultural crops. Further, an insecticide provides a most effective means for achieving the object of preventing infectious diseases from spreading by the extermination of those insects which transmit most of such diseases. Thus, the role played by the insecticide in maintaining an expected higher living standard of mankind is of great significance. Numerous eminent insecticides have heretofore been invented and successfully put into actual use in various fields. On the other hand, however, organochlorine insecticides such as BHC (benzene hexachloride) and DDT [1,1,1-trichloro-2,2-bis(p-chlorophenyl)ethane] have become markedly restricted in their uses on account of the emergence of insect pests resistant to these compounds as well as the problems of environmental pollution and their toxicity to various nontarget organisms. The problem of resistant insects has become increasingly urgent also in other insecticides such as those of the organic phosphate ester type and the carbamate type, which were expected to replace the organochlorine insecticides. Under the circumstances, the advent of a new and more improved insecticides has been eagerly awaited.

Among the properties characterisitc of an improved insecticide, those especially required at present, apart from a high insecticidal activity, are considered to be a low toxicity to nontarget organisms including men and animals, and substantial nonpersistence in order to minimize environmental pollution. Natural pyrethrin possesses a part of the characteristic properties required for an improved insecticide mentioned above, because it has a low toxicity to men and animals and is easily decomposable under outdoor environmental conditions. However, as compared with organic phosphate esters and carbamate compounds, the natural pyrethrin is inferior in insecticidal activity, poorer in residual activity because of too rapid decomposition, and more expensive. For these reasons, the use of natural pyrethrin is limited to such fields as households insect control and the like [E.M. Mrak (1973), "Advantageous and Disadvantages of Pyrethrum", in "PYRETHRUM" (J.E. Casida), Academic Press, New York and London, 1973, pp. 307–311].

A large number of researches were undertaken to make up for the defects of natural pyrethrin and, as a result, several superior synthetic pyrethroid insecticides have been brought forth. Of these, especially those described in Nature, 248, 710 (1974) by M. Elliott et al., Brit Pat. No. 1,413,491, and U.S. Pat. No. 3,996,244 are characterized by (1) outstandingly high insecticidal activity and quick onset, (2) sufficient residual activity without environmental persistence as long-lasting as that of an organochlorine insecticide, (3) comparatively low toxicity to men and animals, and (4) outstanding insecticidal activity against organic phosphate ester- and/or carbamate-resistant insect pests. Consequently, investigations on a worldwide scale are now being undertaken in order to put these synthetic pyrethroids into practical use; in a few districts where the spreading of resistant pests is becoming more significant, actual use has already begun.

However, as shown by J. Miyamoto in Environmental Health Perspectives, 14, 15 (1976), pyrethroid insecticides including natural pyrethrin exhibit, in general, a high toxicity to fishes. Insecticides in no small proportion are used for controlling insect pests in paddy fields, for controlling aquatic insect pests such as larvae of mosquitoes and gnats, and for aerial application over areas scattered with lakes, ponds or rivers. It is predictable that application of the superior synthetic pyrethroid insecticides to the above-noted areas will be restricted owing to their toxicity to fishes. For this reason, reduction of the toxicity of pyrethroids against fishes seems to be an urgent problem.

Considering that it might mark a great step toward a so-called ideal insecticide if there could be successfully developed an insecticide having excellent properties inherent in pyrethroid insecticides together with a low toxicity to fishes, the present inventors conducted extensive studies and, as a result, found that the compounds represented by the general formula (I) have the characteristics which meet the requirements for the intended insecticide. Based on this finding, the present invention has been accomplished.

Although a part of the compounds of this invention have been disclosed, in a broad sense, in DT. Pat. No. 2615435.8, no specific description is found therein with respect to structural formula, physical constants, insecticidal activity, toxicity to fish, and mammalian toxicity of the compounds of this invention.

While having outstanding insecticidal and acaricidal activities, the compounds of this invention are low in toxicity to fishes (for example, carp, killifish, rainbow trout and bluegill). Accordingly, they are suitable for the control of aquatic insect pests such as those inhabiting, for example, paddy fields, lakes and marshes, ponds and pools, rivers, or forest regions scattered therewith. Since they exhibit also a low toxicity to warm-blooded mammals (for example, mice and rats) and a low phytotoxicity to crops, their use fields are very wide. Because of their high insecticidal activity and high residual activity, they are useful in controlling the following wide variety of insect pests, particularly in controlling *Nephotettix cincticeps* which is resistant to conventional insecticides and requires for its control a new insecticide.

Hemiptera;
Delphacidae (planthoppers, delphacids)
(for example, *Sogatella furcifera, Nilaparvata lugens, Laodelphax striatellus*)
Deltocephalidae (leafhoppers)

(for example, *Nephotettix cincticeps, Tettigela viridis, Inazuma dorsalis*)

Aphididae (aphids)

(for example, *Rhopalosiphum padi*)

Pentatomidae (stink bugs, shield bugs)

(for example, *Nezara antennata, Aeschynteles maculatus, Leptocorixa corbetti, Eysarcoris ventralis*)

Lepidoptera (moths and butterflies);

(for example, *Chilo suppressalis, Tryporyza incertuluas, Choristoneura fumiferana, Dendrolimus spectabilis, Susumia exiqua, Cnaphalocrocis medinalis, Sesamia interens*)

Coleoptera (beetles);

(for example, *Oulema oryzae, Echinocnemus squameus*)

Diptera;

(for example, *Agromyza oryzae, Chlorops, oryzae, Hylemya platura, Aedes aegypti, Anopheles stephansi, Culex pipiens pallens*)

Acarina (mites);

(for example, *Tetranychus cinnabarinus, T. urticae, Oligonychus hondoensis*)

The esters of this invention represented by the formula (I) exists in the form of optical isomer due to the asymmetric carbon atoms in both carboxylic acid and alcohol component. An ester prepared by ordinary methods is a mixture of such isomers. All of the isomers are included within the scope of this invention.

A main object of this invention is to provide a novel cyanobenzyl carboxylate (I) which is useful as insecticide, miticide and acaricide.

Another object of this invention is to provide a procedure for preparing such a cyanobenzyl carboxylate (I).

A further object of this invention is to provide an insecticidal or acaricidal composition containing such a cyanobenzyl carboxylate (I).

These and other objects and advantages of the invention will become apparent from the foregoing and the subsequent descriptions.

The cyanobenzyl carboxylate (I) of the present invention may be prepared by various methods, of which typical examples will be described below.

Synthetic method A, by the reaction between an alcohol and a carboxylic acid halide.

An alcohol of the formula,

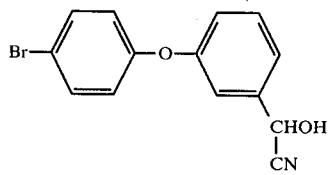

and a trans- or trans-rich-acyl halide, preferably acyl chloride, of the general formula,

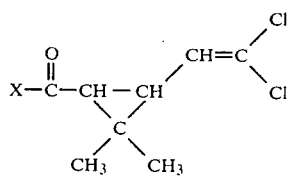

wherein X represents a halogen atom are allowed to react in the presence of an organic tertiary base (for example, triethylamine, pyridine) in an inert solvent (for example, benzene, toluene, ether or hexane) at −30° to 100° C. for 30 minutes to 10 hours to obtain the intended ester.

Synthetic method B, by the reaction between an alcohol and a carboxylic anhydride.

A mixture of an alcohol of the formula,

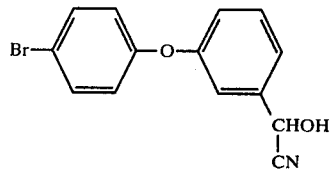

and a trans- or trans-rich-carboxylic anhydride of the formula,

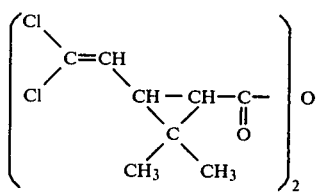

is allowed to react in an inert solvent (for example, benzene, toluene, hexane or acetone) at −20° to 100° C. for 1 to 10 hours to obtain the intended ester.

Synthetic method C, by the reaction between an alcohol and a carboxylic acid.

A mixture of an alcohol of the formula,

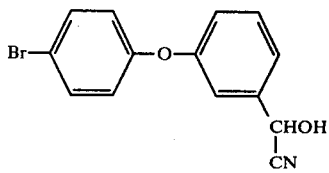

and a trans- or trans-rich-carboxylic acid of the formula,

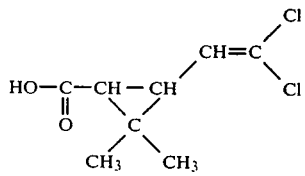

is allowed to react in an inert solvent (for example, benzene, toluene or xylene) in the presence of a dehydrating condensing agent (e.g, dicyclohexylcarbodiimide) at 0° to 150° C. for 30 minutes to 10 hours to obtain the intended ester.

Synthetic method D, by the reaction between a halide and an organic tertiary base salt of a carboxylic acid.

A mixture of a halide of the general formula,

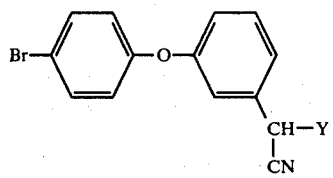

wherein Y is a halogen atom and a trans- or trans-rich-carboxylic acid of the formula,

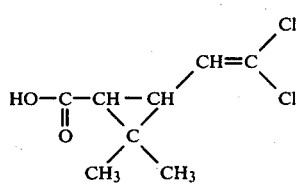

is allowed to react with an organic tertiary base (e.g., triethylamine or trimethylamine) in an inert solvent (for example, acetone, benzene or dioxane) to convert the carboxylic acid into its salt and the whole mixture is allowed to react at 0° to 150° C. for 30 minutes to 10 hours to obtain the intended ester.

Synthetic method E, by the reaction between a halide and an alkali metal salt of a carboxylic acid.

A mixture of a halide of the general formula,

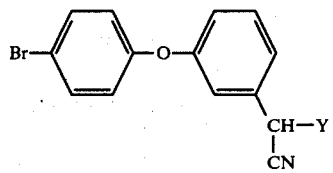

wherein Y is as defined above and an alkali metal salt of a trans- or trans-rich-carboxylic acid of the general formula,

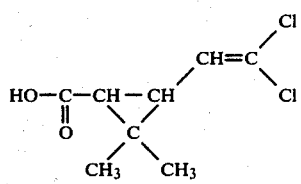

wherein M is an alkali metal (Na, K) is allowed to react in a two-phase system of water and an inert solvent (for example, toluene, heptane or benzene) in the presence of a phase transfer catalyst (for example, tetra-n-butylammonium bromide or benzyltriethylammonium chloride) at 0° to 150° C. for 30 minutes to 10 hours to obtain the intended ester.

Synthetic method F, by the reaction among an aldehyde, an alkali metal cyanide and an acyl halide.

F-1. A mixture of an aldehyde of the formula,

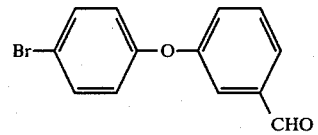

an alkali metal cyanide and a trans- or trans-rich-acyl halide of the general formula,

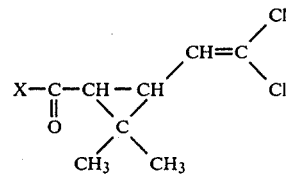

wherein X is as defined above, is allowed to react in an inert solvent (e.g., benzene or toluene) in the presence of a phase transfer catalyst (e.g., dibenzo-18-crown-6 or dicyclohexyl-18-crown-6) at 0° to 150° C. for 30 minutes to 20 hours to obtain the intended ester. F-2. A mixture of an aldehyde of the formula,

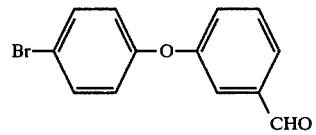

an alkali metal cyanide and a trans- or trans-rich-acyl halide of the general formula,

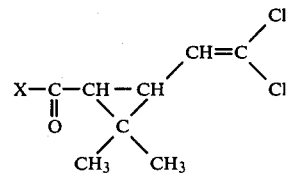

wherein X is as defined above, is allowed to react in a two-phase system of water and an inert solvent (for example, benzene, hexane or toluene) in the presence of a phase transfer catalyst (e.g., tetra-n-butylammonium bromide or benzyltriethylammonium chloride) at 0° to 100° C. for 30 minutes to 10 hours to obtain the intended ester.

The cyanobenzyl carboxylate obtained by any of the above methods can be purified, if necessary, by such a means as chromatography or distillation.

The α-cyanobenzyl alcohol, one of the starting materials, is easily obtained from a corresponding aldehyde by the method described by C. Hilgetag et al. in "Preparative Organic Chemistry", p. 875. The halide can be obtained in good yield from the above alcohol by using a halogenating agent such as phosphorus halide according to the procedure described in "Organic Synthesis", Coll. Vol. III, p. 793, trans- and trans-rich-2,2-dimethyl-3-(2,2-dichlorovinyl)cyclopropanecarboxylic acid can be easily obtained by the method described in Nature, 246 169 (1973) by M. Elliot et al., Pestic. Sci., 5 791 (1974) by M. Elliott et al. and Japanese Patent Publication No. 95045 (1976). The carboxylic acid chloride and the carboxylic anhydride can be obtained in good yields from the carboxylic acid by the method described by R.B. Wagner et al. in "Synthetic Organic Chemistry", p. 546 and p. 558.

Practical and presently preferred embodiments of the preparation of the cyanobenzyl carboxylate (I) are illustratively shown in the following examples.

EXAMPLE 1 (SYNTHETIC METHOD A)

To a solution of 1.82 g (6.0 mmoles) of m- (p-bromophenoxy)-α-cyanobenzyl alochol in 10 ml of anhydrous benzene, was added 0.95 g (12.0 mmoles) of pyridine. To the resulting mixture, with stirring and maintaining a temperature below 5° C. in an ice bath, was added dropwise a solution of 1.37 g (6.0 mmoles) of dl-trans-2,2-dimethyl-3-(2,2-dichlorovinyl) cyclopropanecarbonyl chloride in 5 ml of anhydrous benzene. After the addition was completed, the reaction mixture was allowed to react at room temperature and stirred overnight. After dissolution of the precipitated pyridine hydrochloride by addition of water to the reaction mixture, the aqueous layer was separated. The organic layer was washed with 5% hydrochloric acid, saturated aqueous sodium hydrogencarbonate solution and then saturated aqueous sodium chloride solution. After drying over anhydrous sodium sulfate, the organic layer was concentrated under reduced pressure. The residue was chromatographed on silica gel to give 2.76 g of m-(p-bromophenoxy)-α-cyanobenzyl dl-trans-2,2-dimethyl-3-(2,2-dichlorovinyl)-cyclopropanecarboxylate as a pale yellow liquid (yield 93%).

EXAMPLE 2 (SYNTHETIC METHOD B)

To a solution of 1.82 g (6.0 mmoles) of m- (p-bromophenoxy)-α- cyanobenzyl alcohol in 10 ml of toluene, was added 2.40 g (6.0 mmoles) of dl-trans-rich(cis-/trans=20/80)-2,2-dimethyl-3-(2,2-dichlorovinyl(cyclopropane-carboxylic anhydride. The resulting mixture was stirred at room temperature for 3 hours and then heated under reflux for an hour. After cooling, the reaction mixture was washed with a 5% aqueous sodium hydroxide solution to remove the carboxylic acid. The organic layer was washed with saturated aqueous sodium chloride solution and dried over anhydrous sodium sulfate. The solvent was evaporated under reduced pressure to give 2.85 g of m-(p-bromopenoxy)-α-cyanobenzyl dl-trans-rich(cis/trans=20/80)-2,2-dimethyl-3-(2,2-dichlorovinyl)cyclopropane-carboxylate as an orange liquid (yield 96%).

EXAMPLE 3 (SYNTHETIC METHOD C)

To a solution of 1.52 g (5.0 mmoles) of m-(p-bromophenoxy)-α-cyanobenzyl alcohol and 1.05 g (5.0 mmoles) of dl-trans-2,2-dimethyl-3-(2,2-dichlorovinyl)-cyclopropanecarboxylic acid in 10 ml of anhydrous benzene, was added 2.06 g (10 mmoles) of dicyclohexylcarbodiimide. The mixture was stirred overnight. The precipitated dicyclohexylurea was removed by filtration and the filtrate was concentrated. The residue was chromatographed on silica gel to give 2.28 g of m-(p-bromophenoxy)-α-cyanobenzyl dl-trans-2,2-dimethyl-3-(2,2-dichlorovinyl)cyclopropanecarboxylate as a pale yellow liquid (yield 92%).

EXAMPLE 4 (SYNTHETIC METHOD D)

To a solution of 2.20 g (6.0 mmoles) of m-(p-bromophenoxy)-α-cyanobenzyl bromide and 1.50 g (7.2 mmoles) of dl-trans-2,2-dimethyl-3-(2,2-dichlorovinyl) cyclopropanecarboxylic acid in 20 ml of acetone with stirring at 15° to 20° C., was added dropwise a solution of 0.81 g (8.0 mmoles) of triethylamine in 5 ml of acetone. Thereafter, the mixture was refluxed for 2 hours and then allowed to cool to room temperature. The reaction mixture was filtered to remove the precipitated triethylamine hydrobromide and the filtrate was concentrated under reduced pressure. The residue was chromatograhed on silica gel to give 2.58 g of m-(p-bromophenoxy)-α-cyanobenzyl dl-trans-2,2-dimethyl-3-(2,2-dichlorovinyl)cyclopropanecarboxylate as a pale yellow liquid (yield 87%).

EXAMPLE 5 (SYNTHETIC METHOD E)

A solution of 2.20 g (6.0 mmoles) of m-(p-bromophenoxy)-α-cyanobenzyl bromide in 10 ml of toluene and a solution of 1.66 g (7.2 mmoles) of sodium dl-trans-rich(cis/trans=20/80)-2,2-dimethyl-3-(2,2-dichlorovinyl)-cyclopropanecarboxylate in 7 ml of water were mixed. After addition of 0.081 g (0.25 mmole) of tetra-n-butylammonium bromide, the mixture was stirred for 4 hours at 70° to 80° C. The reaction mixture was washed with saturated aqueous sodim chloride solution and dried over anhydrous sodium sulfate. The solvent was evaporated under reduced pressure to give 2.88 g of m-(p-bromophenoxy)-α-cyanobenzyl dl-trans-rich(cis/trans=20/80)-2,2-dimethyl-3-(2,2-dichlorovinyl)cyclopropanecarboxylate as an orange liquid (yield 97%).

EXAMPLE 6 (SYNTHETIC METHOD F-1)

To a suspension of 0.44 g (9.0 mmoles) of sodium cyanide and 0.10 g of dibenzo-18-crown-6 in 10 ml of anhydrous benzene, was added dropwise, with stirring at room temperature, a solution of 1.66 g (6.0 mmoles) of m-(p-bromophenoxy)benzaldehyde and 1.43 g (6.30 mmoles) of dl-trans-2,2-dimethyl-3-(2,2-dichlorovinyl)-cyclopropanecarbonyl propanecarbonyl chloride in 10 ml of anhydrous benzene. Thereafter, the mixture was further stirred overnight. The reaction mixture was washed with saturated aqueous sodium chloride solution and the solvent was evaporated. The residue was chromatographed on silica gel to give 2.82 g of m-(p-bromophenoxy)-α-cyanobenzyl dl-trans-2,2-dimethyl-3-(2,2-dichlorovinyl)cyclopropanecarboxylate as a pale yellow liquid (yield 95%).

EXAMPLE 7 (Synthetic method F-2)

To a solution of 0.37 g (7.5 mmoles) of sodium cyanide and 0.012 g (0.037 mmoles) of m-phenoxybenzyltriethylammonium chloride in 5 ml of water, was added dropwise, with stirring at room temperature, a solution of 1.39 g (5.0 mmoles) of m-(p-bromophenoxy)benzaldehyde and 1.19 g (5.25 mmoles) of dl-trans-2,2-dimethyl-3-(2,2-dichlorovinyl)cyclopropanecarbonyl chloride in 10 ml of toluene. The resulting mixture was stirred for 5 hours at room temperature and then washed with saturated aqueous sodium chloride solution. The organic layer was dried over anhydrous sodium sulfate and the solvent was evaporated to give 2.42 g of m-(p-bromophenoxy)-α-cyanobenzyl dl-trans-2,2-dimethyl-3-(2,2-dichlorovinyl)cyclopropanecarboxylate as an orange liquid (yield 98%).

TABLE 1

| Compound No. | Structural formula | Refractive index | Elementary analysis |
|---|---|---|---|
| 1 | [structure shown] [m-(p-bromophenoxy)-α-cyanobenzyl dl-trans-2,2-dimethyl-3-(2,2-dichlorovinyl)-cyclopropanecarboxylate] | $n_D^{25.0}$ 1.5774 | Found C:53.18%, H: 3.92%, N: 2.96% Calc'd C:53.36%, H: 3.66%, N: 2.83% |
| 2 | [m-(p-bromophebnoxy)-α-cyanobenzyl dl-trans-rich (cis/trans = 20/80)-2,2-dimethyl-3-(2,2-dichlorovinyl)cyclopropane-carboxylate] | $n_D^{23.0}$ 1.5793 | Calc'd C:53.20% H: 3.78% N: 3.01% |

In applying the compound of this invention as an insecticide or acaricide, it can be employed as such without blending with other ingredients, but generally it is used in the form of pesticidal composition by blending with a carrier to improve its handling quality as a pest controlling agent; and such a composition may be further diluted prior to use, if necessary.

In preparing pesticidal compositions, the compound of this invention may be formulated in a manner similar to that used in customary pesticides by use of techniques well known to those skilled in the art and no other special precautions are necessary. The compound of this invention may be employed for the intended use in any form such as emulsifiable concentrate, wettable powder, dust, granule, fine granule, oil preparation, aerosol, heating fumigant (mosquito coil, electrically heating mosquito mat), fuming preparation such as fogging, non-heating fumigant, poisonous bait, etc.

The compounds of this invention may be used in combinations of two or more members to enhance the insecticidal and acaridcidal activity. The activity may also be enhanced by incorporating with synergists for pyrethroids, such as α-[2-(2-butoxyethoxy)ethoxy]-4,5-methylenedioxy-2-propyltoluene (referred to as "piperonyl butoxide"), 1,2-methylenedioxy-4-[2-(octylsulfinyl)-propyl]benzene,4-(3,4-methylenedioxyphenyl)-5-methyl-1,3-dioxane, N-(2-ethylhexyl)-bicyclo[2,2,1-]hepta-5-ene-2,3-dicarboxyimide, octachlorodipropyl ether, isobornyl thiocyanoacetate, and other known synergists effective for pyrethrin.

Although highly resistant to sunlight, heat and oxidation, the compound of this invention may be further stabilized against severe oxidative conditions by incorporating with a suitable amount of stabilizers. Suitable stabilizers are antioxidants and ultraviolet absorbers including phenol derivatives and bisphenol derivatives such as BHT[*1] and BHA[*2]; arylamines such as phenyl-α-naphthylamine, phenyl-β-naphthylamine and phenetidine-acetone condensate; and benzophenone compounds.

*1 BHT: 2,6-di-tert-butyl-4-methylphenol; 6 *2 BHA:2-tert-butyl-4-methoxyphenol.

The insecticidal and/or acaricidal compositions according to this invention contain 0.001 to 80.0%, preferably 0.01 to 50% by weight of an active ingredient.

Practical embodiments of the insecticidal or acaricidal composition according to this invention are illustratively shown in the following example, wherein parts and percents are by weight.

FORMULATION EXAMPLE 1

10 Parts of the compound (1) or (2) of this invention were mixed with 15 parts of "Sorpol 3005X" (a mixture of nonionic surfactant (polyoxyethylene phenyl phenol derivative) and anionic surfactant (alkyl aryol sulfonate)) and 75 parts of xylene. The mixture was thoroughly stirred, mixed, and dissolved to obtain respective 10% emulsifiable concentrate.

FORMULATION EXAMPLE 2

Each 0.2 part of the compound (1) or (2) of this invention was dissolved in 20 parts of acetone, admixed with 99.8 parts of 300-mesh clay, stirred thoroughly, and freed from the acetone by evaporation to yield 0.2% dust preparation of the compound.

FORMULATION EXAMPLE 3

Each 50 parts of the compound (1) or (2) of this invention was well mixed with 5 parts of "Sorpol 5029-0" (a special anionic surfactant), admixed with 45 parts of 300-mesh diatomaceous earth, and thoroughly mixed in a grinding mill to obtain 50% wettable powder of the compound.

FORMULATION EXAMPLE 4

To each 2 parts of the compound (1) or (2) of this invention was added 2 parts of sodium ligninsulfonate (a binder) followed by 96 parts of clay (an extender). The mixture was thoroughly blended in a grinding mill, admixed with water in an amount of 10% of the resulting mixture, again mixed thoroughly, then granulated by means of a granulator, and dried in air stream to obtain 2% granule of the compound.

FORMULATION EXAMPLE 5

0.5 Part of the compound (1) or (2) of this invention was dissolved in illuminating kerosene to make a total of 100 parts to obtain a 0.5% oil spray.

FORMULATION EXAMPLE 6

A mixture of 0.5 part of the compound (1) or (2) of this invention and 0.5 part of piperonyl butoxide was dissolved in purified kerosene to make a total of 100 parts to obtain a 0.5% oil spray.

The outstanding insecticidal and acaricidal activity and surprisingly low toxicity to mammals and fishes of the compounds of this invention are illustrated below with reference to Test Examples. In Test Examples, reference compositions were prepared similarly to the test compositions using known compounds shown in Table 1.

TABLE 1

| Reference compound No. | Structure | Literature |
|---|---|---|
| (A) | m-(p-bromophenoxy)-α-cyanobenzyl dl-cis, trans-2,2-dimethyl-3-(2,2-dichlorovinyl)cyclopropane-carboxylate | DT-OS 2615435 |
| (B) | m-phenoxybenzyl dl-cis,trans chrysanthemate | USP 3666789 |
| (C) | m-phenoxybenzyl dl-cis,trans-2,2-dimethyl-3-(2,2-dichlorovinyl)cyclopropanecarboxylate | Brit. Pat. No. 1,413,491 |
| (D) | m-phenoxy-α-cyanobenzyl dl-cis,trans-2,2-dimethyl-3-(2,2-dichlorovinyl)-cyclopropanecarboxylate | Brit. Pat. No. 1,413,491 |
| (E) | m-(p-fluorophenoxy)-α-cyanobenzyl dl-cis,trans-2,2-dimethyl-3-(2,2-dichlorovinyl)cyclopropanecarboxylate | USP 3973036 |
| (F) | CH₃NHCOO—(benzene ring with CH₃ groups) | T. Iwata et al. "J. Eco. Ento. 65(3) 643(1972) |
| (G) | Pyrethrins | F. B. LaForge et al; "J. Am. Chem. Soc., 58, 1777 (1936)" |

TEST EXAMPLE 1

The compound (1) of this invention were tested for toxicity to fishes (fish toxicity), insecticidal activity, and mammalian toxicity.

[Experimental method]

1. Fish toxicity test.

Ten member group of *Oryzias latipes* (0.2–0.3 g/fish) was released in a 10-liter glass vessel containing 10 liters of a test preparation which was dissolved or suspended in "Tween 80" and diluted successively with dechlorinated tap water. After 48 hours, the dead and alive were counted to determine median tolerance limit (48 hours) [$TL_{m48}$ (ppm)] value.

2. Insecticidal activity test.

Test emulsion preparations were prepared in the same manner as in Formulation Example 1.

Activity to *Nephotettix cinciticips*

The test insect was resistant to carbamates (hereinafter referred to as R-type). The active ingredient content of test preparation was varied in 4 levels within the range of 500 to 1 ppm. The test preparation was sprayed over 180-ml plastic cups grown with rice plant one-month old from sowing and placed on a turn table, the application rate having been 15 cc/2 cups. After air drying, the plant was covered with a wire-screen cage. A group of 15 female adults of R-type *Nephotettix cincticeps* was released in each cage and kept at 26° C. in an artificial climate condition. After 24 hours, the dead and alive were observed. The median lethal concentration [$LC_{50}$ (ppm)] was calculated from the mortality determined by 3-repetition test.

[Results]

The fish toxicity and insecticidal activity of the compounds of this invention were as shown in Table 2. In order to make more clear the low fish toxicity and the high activity to target insects, which are charcteristic of the compounds of this invention, a fish safety coefficient was calculated from the test results of fish toxicity and insecticidal activity by the following equation and shown in Table 2.

$$\text{Fish safety coefficient} = \frac{\text{Fish toxicity } (TL_{m48} \text{ (ppm)})}{\text{Insecticidal activity } (LC_{50} \text{ (ppm)})}$$

In the case of *N. cincticeps*, calculation was based on a hyothetical concentration of the test compound in water obtained by assuming that a test preparation of the active ingredient content corresponding to $LC_{50}$ (ppm) was sprayed over a submerged paddy field, 5 cm in depth of water, at a rate of 100 liters per 10 ares and total active ingredient was absorbed by the water.

For example, in the case of compound (1) of this invention, the quantity of water per 10 ares of the submerged paddy field, 5 cm in depth of water, is 50 tons. If a preparation of the active ingredient content equivalent to $LC_{50}$ (ppm) of the compound (1) is sprayed at a rate of 100 liters per 10 ares, the concentration of the compound (1) in the water is 0.007 ppm. The fish toxicity [$TL_{m48}$] of the compound (1) is 6.0 ppm. The fish safety coefficient (857.1) is obtained by dividing 6.0 by 0.007.

TABLE 2

| Compound No. | Fish toxicity $TL_{m48}$ (ppm) (a) | Nephotettix cincticeps $LC_{50}$ (ppm) | Nephotettix cincticeps Concentration of active ingredient in water (b) | Safety coefficient to fishes (a)/(b) |
|---|---|---|---|---|
| (1) | 6.0 | 3.5 | 0.007 | 857.1 |
| (A) | 0.9 | 8.0 | 0.016 | 56.3 |
| (C) | 0.027 | 18.0 | 0.036 | 0.8 |
| (D) | 0.026 | 5.0 | 0.01 | 2.6 |
| (E) | 0.003 | 5.0 | 0.01 | 0.3 |
| (F) | 11.9 | 350.0 | 0.7 | 17.0 |

Note
(1): Present compound (trans isomer content, 99% or more)
(A), (C), (D), (E), (F): Reference compounds [(A), (C), (D) and (E), a mixture of almost the same amounts of the cis and trans isomers].

It is apparent from Table 1 that the present compound (1) is higher in insecticidal activity than the reference compounds (A), (C) and (F), and lower in toxicity to killifish than the reference compounds (A), (C), (D) and (E). Also, the safety coefficient to fishes of the present compound, calculated from the values in Table 2, shows a very high value as compared with that of the reference compounds.

From the above results, it may be concluded that the present compound has a clearly high selective toxicity as compared with the reference compounds.

TEST EXAMPLE 2

The present compound (1) and (2) were mixed in a predetermined proportion, formulated into an emulsifiable concentrate according to Formulation Example 1 and diluted with water so that the amount of active ingredient was 10 ppm.

The test preparation was sprayed over rice plant in tillering stage planted in a 1/10,000 are Wagner pot, at a rate of 15 cc per pot. After airdrying, the plant was covered with a wire-screen cage into which were released 15 female adults of R-type *Nephotettix cincticeps*. The pot was kept at 26° C. in an artificial climate condition. After 24 hours, the dead and alive were observed and the mortality was obtained by 3-repetition test.

TABLE 3

| Compounds | Rate (%) of mixture of dl-trans and dl-cis | | | Reference Compound (B) |
|---|---|---|---|---|
| Compound (1) of this invention | 99 | 80 | 50 | |
| Compound (2) of this invention | 1 | 20 | 50 | |
| Mortality (%) | 100 | 100 | 70 | 10 |

TEST EXAMPLE 3

The present compounds (1) and (2) were mixed in predetermined proportion, and Tween 80 was added thereto. After stirring, the mixture was diluted with dechlorinated tap water so that the amount of active ingredient was 1 ppm. Ten liters of the test solution was placed in a 10-liter glass vessel and 10 killifishes (*Oryzias latipes*) were liberated therein. After 48 hours, the survival rate was examined by 3 repetitions.

TABLE 4

| Compounds | Rate (%) mixture of dl-trans and dl-cis | | |
|---|---|---|---|
| Compound (1) of this invention | 99 | 80 | 50 |
| Compound (2) of this invention | 1 | 20 | 50 |
| Average survival rate (%) | 100 | 100 | 41 |

TEST EXAMPLE 4

The emulsion preparation containing the compound (1) of this invention, described in Formulation Example 1, was diluted with water. The active ingredient content of the test prepartion was varied in 4 levels within the range of 150 to 10 ppm. The test preparation was sprayed over 180 ml plastic cups grown with rice plant and placed on a turn table the application rate having been 15 cc/2 cups. After air drying, the plant was covered with a wire-screen cage. A group of 15 female adults of *Laodelphax striatellus* was released in each cage and kept at 26° C. in an artificial climate condition. After 24 hours, the dead and alive were observed. The median lethal concentration [$LC_{50}$ (ppm)] was calculated from the mortality determined by 3-repetition test.

TABLE 5

| Compound | $LC_{50}$ (ppm) |
|---|---|
| Compound (1) of this invention | 70.0 |

TEST EXAMPLE 5

The present compound (1) was diluted with acetone to four different concentrations.

The acetone dilute solution was topically applied to the ventral thorax of WHO strain housefly female adults (*Musca domestica*), at a rate of 0.5 μl/adult by means of a microsyringe.

The adults were then liberated in a plastic cup of 12 cm in diameter and given a 1% sugar water. After 24 hours, the dead and alive were examined. The median lethal does ($LD_{50}$ μg/adult) was obtained from the mortality of 50 adults per group.

TABLE 6

| Compound | $LD_{50}$ μg/adult |
|---|---|
| Present compound (1) | 0.035 |

TEST EXAMPLE 6

The emulsifiable concentrate of the present compound (1) prepared in Formulation Example 1 was diluted with water so that the concentration of active ingredient was 500 ppm. Five rice seedlings which had elapsed 10 days after sowing were dipped in the dilute solution and air-dried. The rice seedlings and 10 third instar larvae of rice stem borer (*Chilo suppressalis*) were placed in a plastic cup (diameter 5.5 cm, height 3.5 cm) which was then placed in an artificial climate chamber kept at 26° C. After 10 days, the dead and alive of the larvae were examined, and it was found that 100% of the larvae could be killed.

TEST EXAMPLE 7

The emulsifiable concentrate of the present compound (1) prepared in Preparation example 1 was diluted with distilled water so that the concentration of active ingredient was 0.1 ppm. One hundred milliliters of the dilute solution was placed in a 180-ml plastic cup, and 30 full grown larvae of Aedes aegypty (*Culex pipiens pallens*) were liberated therein. After 24 hours, 100% of the larvae could be killed.

TEST EXAMPLE 8

The emulsifiable concentrate of the present compound (1) prepared in Formulation Example 1 was diluted with water so that the concentration of active ingredient was 500 ppm. The dilute solution was then thoroughly sprayed on rice plants (grown in a 1/10,000 are Wagner's pot) on which carmine mites (*Tetranychus cinnabarinus*) in all stages were made parasitic. After 10 days, the degree of damage by the carmine mites was examined, and it was found that the spreading of damage could be prevented.

TEST EXAMPLE 9 (RESIDUAL EFFECT TEST)

The emulsifiable concentrate of the present compound (1) prepared in Formulation Example 1 was diluted with water so that the concentration of active ingredient was 400 ppm. Thereafter, 20 cc of the dilute solution was sprayed on rice plants grown in a 1/10,000 are Wagner's pot. The rice plants were air-dried and covered with a wire-screen cage, and 15 female adults of green rice leafhopper (*Nephotettix cincticeps*) were liberated therein. After 24 hours, the dead and alive were examined to obtain mortality. In order to examine the residual effect, the pot was then left as it was for 7 days, and the test insects were liberated in the same manner as above. After 24 hours, the mortality was examined. The experiment was carried out in a greenhouse and the number of repetitions was three.

TABLE 7

| Compound | Mortality (%) | |
|---|---|---|
| | Effect immediately after treatment | Effect 7 days after treatment |
| Present compound (1) | 100 | 100 |
| Reference compound (F) | 100 | 0 |
| Reference compound (G) | 100 | 0 |

TEST EXAMPLE 10 (TOXICITY TEST)

The present compound (1) was dissolved or suspended in a corn oil, and the resulting solution was orally administered to a male mouse (18 to 22 g) at a rate of 0.2 ml/10 g body weight. After 24 hours, the mortality was examined to obtain the median lethal dose ($LD_{50}$ mg/kg).

TABLE 8

| Compound | $LD_{50}$ mg/kg |
|---|---|
| Present compound (1) | >2,000 |
| Reference compound (C) | 650 |
| Reference compound (D) | 112 |
| Reference compound (E) | 300 |
| Reference compound (F) | 60 |
| Reference compound (G) | 370 |

TEST EXAMPLE 11

The dust of the present compound (1) prepared in Formulation Example 2 was diluted with dechlorinated tap water to a predetermined concentration of active ingredient. Ten liters of the test solution was placed in a 10-liter glass vessel, and 10 killifishes Oryzias latipes) were liberated therein. After 48 hours, the dead and alive were examined, and $TL_{m48}$ (ppm) was calculated from the concentration of active ingredient.

TABLE 9

| Compound | $TL_{m48}$ (ppm) |
|---|---|
| Present compound (1) | >10 |

TEST EXAMPLE 12

Toxicity to carps was tested according to the test method for toxicity to fishes described in Test Example 11, and $TL_{m48}$ (ppm) values after 48 hours were obtained.

TABLE 10

| Compound | $TL_{m48}$ (ppm) |
|---|---|
| Present compound (1) | >10 |
| Reference compound (D) | ≦0.01 |

TEST EXAMPLE 13

The wettable powder of the present compound (1) prepared in Formulation Example 3 was diluted with water so that the concentration of active ingredient was 100 ppm. Soil was placed in a plastic box [5m×5m×2m (deep)] to a level of 50 cm from the bottom, and rice plants about 50 cm high were transplanted at intervals of 50 cm. Water was then placed in the bos so that water depth was 5 cm, and 20 killifishes (Oryzias latipes) were liberated therein. Thereafter, the above dilute solution was sprayed on the box at a rate of 100 liter/10 are. The solution fell on the rice plants as well as on the water surface.

One hour after treatment, 100 female adults of green rice leafhopper (Nephotettix cincticeps) were liberated in the box which was immediately covered with a net. After 48 hours, no green rice leafhoppers were found, whereas all of the killifishes were alive.

What is claimed is:

1. m-(p-Bromophenoxy)-α-cyanobenzyl trans- or trans-rich-2,2-dimethyl-3-(2,2-dichlorovinyl)cyclopropanecarboxylate.

2. A low mammalian toxic and/or low fish toxic insecticide and/or acaricide composition which comprises as an active ingredient an insecticidally and/or acariciadally effective amount of the compound according to claim 1 and an inert carrier.

3. The low mammalian toxic and/or low fish toxic insecticide and/or acaricide composition according to claim 2, wherein the amount of the active ingredient is 0.001 to 80.0% by weight.

4. A method for controlling an insect and/or acaride which comprises applying an insecticidally and/or acaricidally effective amount of the compound according to claim 1 to the insect and/or acarid.

5. The method according to claim 4, wherein the insect is one living in an aquatic place.

* * * * *